United States Patent [19]
Hansen et al.

[11] Patent Number: 6,107,341
[45] Date of Patent: Aug. 22, 2000

[54] AQUEOUS MITICIDE CONTAINING BENZYL BENZOATE

[75] Inventors: Eric J. Hansen, Ada; Jesse J. Williams, Hudsonville, both of Mich.

[73] Assignee: Bissell Homecare, Inc., Grand Rapids, Mich.

[21] Appl. No.: 09/184,456

[22] Filed: Nov. 2, 1998

Related U.S. Application Data

[60] Provisional application No. 60/068,270, Dec. 19, 1997.

[51] Int. Cl.$^7$ .................................................. A01N 37/10
[52] U.S. Cl. ............................................................ 514/544
[58] Field of Search ...................... 514/112, 544

[56] References Cited

U.S. PATENT DOCUMENTS

| | | | |
|---|---|---|---|
| 3,808,319 | 4/1974 | Kanfoush | 424/308 |
| 3,996,379 | 12/1976 | Mihailovski | 424/308 |
| 4,666,940 | 5/1987 | Bischoff et al. | 514/544 |
| 4,806,526 | 2/1989 | Green | 514/23 |
| 4,857,551 | 8/1989 | Tapolczay et al. | 514/532 |
| 4,877,811 | 10/1989 | Anthony et al. | 514/522 |
| 5,839,155 | 11/1998 | Berglund et al. | 15/31 |
| 5,843,981 | 12/1998 | Miller | 514/421 |
| 5,854,288 | 12/1998 | Katsuda et al. | 514/594 |
| 5,905,066 | 5/1999 | Zocchi et al. | 510/280 |
| 5,916,917 | 6/1999 | Suh et al. | 514/544 |
| 5,942,482 | 8/1999 | Zocchi et al. | 510/280 |
| 5,985,814 | 11/1999 | Zocchi et al. | 510/280 |
| 5,990,157 | 11/1999 | Zocchi et al. | 514/464 |

FOREIGN PATENT DOCUMENTS

| | | |
|---|---|---|
| 566979 | 10/1993 | European Pat. Off. . |
| 617612 | 9/1997 | European Pat. Off. . |
| 60042314 | 3/1985 | Japan . |
| 601663804 | 8/1985 | Japan . |
| 61136600 | 6/1986 | Japan . |
| 2076707 | 4/1997 | Russian Federation . |
| 567744 | 8/1977 | U.S.S.R. . |

*Primary Examiner*—Jose' G. Dees
*Assistant Examiner*—Alton Pryor
*Attorney, Agent, or Firm*—Rader, Fishman, Grauer & Mc Garry, An Office of Rader, Fishman & Grauer PLLC

[57] ABSTRACT

Compositions and methods for killing dust mites are disclosed. The disclosed miticides are aqueous mixtures composed of benzyl benzoate in an amount effective for killing dust mites and a solvent having a high affinity for benzyl benzoate and for water. The amount of solvent is sufficient to maintain a stable dispersion of benzyl benzoate in the aqueous mixture. Benzyl alcohol, which is itself a miticide, is an especially useful solvent. The miticide optionally contains at least one surfactant, which along with the solvent, helps maintain a stable dispersion of benzyl benzoate in the aqueous mixture. The aqueous mixture is applied to surfaces of household furnishings including bedding, carpeting, and upholstery, using conventional liquid application techniques. An important aspect of the present invention is that the miticide is a fully aqueous solution that, unlike available miticides, contains no solid particles for dispersing the benzyl benzoate.

33 Claims, No Drawings

AQUEOUS MITICIDE CONTAINING BENZYL BENZOATE

CROSS REFERENCE TO RELATED APPLICATION

This invention claims the benefit of U.S. provisional patent application Serial No. 60/068,270, filed Dec. 19, 1997.

FIELD OF THE INVENTION

This invention relates to methods and compositions for killing dust mites.

BACKGROUND OF THE INVENTION

One of the most potent indoor allergens is house dust contaminated with dust mites. It is thought that dust mites may be an important factor in between 50 to 80 percent of all asthma cases, and contributes to countless cases of eczema, hay fever and other allergic reactions. Symptoms of hypersensitivity to dust mites include sneezing, itching, watery eyes, as well as headaches, fatigue and depression. Respiratory ailments associated with dust mites result from contact with proteins in the digestive juices from the dust mite gut which are carried on the fecal pellets, and exposure to dust mites in the first, critical year of life can trigger a lifelong allergy. There is no known cure for dust mite allergies, only prevention through the control of dust mite levels.

Beds are the primary habitat for dust mites. A typical mattress may harbor anywhere from 100,000 to 10 million mites. Nearly ten percent of a well-used pillow is composed of dead mites and their droppings. Mites prefer warm, moist surroundings such as the top surfaces of a mattress while the human occupant is asleep, and their major source of food is the dead skin shed from humans and their pets. Significant numbers of mites can also be found in bedroom carpeting and household upholstery.

Currently, at least two products are commercially available for control of dust mites. They contain benzyl benzoate and/or tannic acid as active ingredients. Benzoic acid esters, such as benzyl benzoate, are effective agents for killing house dust mites based on laboratory testing and field evaluations. Benzyl benzoate does not pose a serious health risk when used in the amounts needed to kill mites because it is rapidly metabolized to hippuric acid, which is excreted in urine.

Although benzyl benzoate is an effective miticide, its use is not without problems. For cost and safety reasons, benzyl benzoate is diluted when used to control dust mites. However, benzyl benzoate is insoluble in water, and is therefore ineffective as an aqueous spray. In commercial miticides, benzyl benzoate is adsorbed on solid particles to aid in its dispersion. The resulting dispersion is applied as either a moist powder or foam to carpets and bedding. One drawback is that the moist powder tends to clump together, so that it is difficult to apply evenly. Another drawback is that solid-stabilized benzyl benzoate miticides leave behind a powdery residue that is easily removed by vacuuming, which reduces its effectiveness.

The present invention is directed to overcoming, or at least minimizing, one or more of the problems set forth above.

SUMMARY OF THE INVENTION

According to the invention, an aqueous mixture comprises benzyl benzoate in an amount effective for killing dust mites and a solvent having a high affinity for benzyl benzoate and for water. The amount of solvent is sufficient to maintain a stable dispersion of benzyl benzoate in the aqueous mixture. Useful solvents include aliphatic alcohols, aromatic alcohols, and glycol ethers. Benzyl alcohol, which is itself a miticide, is an especially useful and preferred solvent in the invention.

Further according to the invention, an aqueous mixture comprises benzyl benzoate in an amount effective for killing dust mites, a solvent that is at least partially soluble in both benzyl benzoate and water, and a surfactant. The amount of surfactant and solvent is sufficient to maintain a stable dispersion of benzyl benzoate in the aqueous mixture. Useful surfactants include lipophillic, hydrophobic, anionic, non-ionic, cationic and amphoteric compounds.

Still further according to the invention, a method of controlling dust mites comprises the step of applying to a surface an aqueous mixture of an effective amount of benzyl benzoate for killing dust mites, a solvent such as benzyl alcohol, and an optional surfactant. The aqueous mixture is applied to surfaces of household furnishings including bedding, carpeting, and upholstery, using conventional liquid application techniques.

An important aspect of the invention is that the miticide is a fully aqueous solution that, unlike heretofore available miticides, contains no solid particles for dispersing the benzyl benzoate. As a result, the invention does not leave behind particulate residue following application and is easy to apply with conventional deep cleaning equipment. In order to kill dust mites, existing miticides rely on dust mites ingesting the solid carrier particles. Because these particles are easily removed by vacuuming, miticidal activity decreases sharply after the carpet is cleaned. In contrast, residual miticidal activity in the present invention is not significantly affected by vacuuming since the active ingredients in the miticide are adsorbed on the carpet fibers. Furthermore, since the aqueous mixture can be packaged as a liquid concentrate, it is easier to store, handle and apply than miticides adsorbed on bulky solid particles.

DESCRIPTION OF THE PREFERRED EMBODIMENTS

The disclosed miticide comprises an aqueous mixture of benzyl benzoate and a solvent. Because benzyl benzoate is insoluble in water, it is combined with sufficient solvent to maintain a stable dispersion of benzyl benzoate in the aqueous mixture. The aqueous mixture can then be applied to surfaces that may harbor dust mites—carpets, bedding, upholstery, and the like—using conventional techniques. Since the solvent obviates the need for a solid carrier, the disclosed miticide does not leave behind particulate residue following application.

The aqueous benzyl benzoate mixture can be an emulsion: a colloidal dispersion of benzyl benzoate in water and solvent. Or, it can be a true solution, in which the benzyl benzoate, solvent, and water are uniformly dispersed at the molecular level. In either case, once benzyl benzoate is uniformly dispersed in the aqueous mixture, the solvent helps maintain a stable dispersion by preventing benzyl benzoate from coalescing prior to application. Ideally, the aqueous miticide mixtures are transparent.

Suitable solvents show a high affinity for benzyl benzoate and for water and are therefore at least partially soluble in both. Examples of useful solvents include aliphatic alcohols, aromatic alcohols, glycol ethers, or combinations of aliphatic alcohols, aromatic alcohols and glycol ethers. Specific examples thus include ethyl alcohol, isopropyl alcohol, and benzyl alcohol. Benzyl alcohol is especially useful because, like benzyl benzoate, it is effective in killing dust mites.

In aqueous miticides comprising benzyl benzoate, benzyl alcohol, and water, the ratio of benzyl alcohol to benzyl benzoate is typically in a range of about 5:1 to about 1:5 by weight. Generally, the ratio depends on the total amount of benzyl benzoate and benzyl alcohol present in the aqueous mixture, and on the presence of any additional components, such as surfactants, deodorants, colorants, anti-allergenic compounds, and the like. Studies show that, in the absence of surfactants, a 2:1 weight ratio of benzyl alcohol to benzyl benzoate works well for most commercially viable, safe, and efficacious levels of benzyl alcohol and benzyl benzoate. For the purposes of this disclosure, a miticide is considered effective if it kills at least 80 percent of a given dust mite population following application.

Generally, aqueous miticides comprising from about 0.01% to about 5% benzyl benzoate and benzyl alcohol solution by weight are effective in killing dust mites. Because the aqueous mixtures are effective over such a wide range of benzyl benzoate and benzyl alcohol concentrations, the aqueous miticides can be packaged as concentrates, which are diluted with water prior to application. Such concentrates will normally contain from about 1.0% to about 2.5% benzyl benzoate and benzyl alcohol solution. For example, research shows that a 2.5 wt. % aqueous mixture of a 2:1 weight ratio of benzyl alcohol to benzyl benzoate can kill about 95% of a dust mite population following application.

In addition to benzyl benzoate and solvent, the miticide may also contain one or more surfactants. Surfactants help maintain a stable colloidal dispersion of benzyl benzoate in the aqueous mixture. By adding the proper amount of surfactant and solvent, the benzyl benzoate forms a stable, transparent aqueous emulsion. If packaged as a concentrate, the clear benzyl benzoate emulsion will usually turn cloudy or white when diluted with water.

Common surfactants can be anionic, non-ionic, cationic, lipophillic, hydrophobic, or amphoteric substances commonly used in textile cleansers. Examples of anionic surfactants include sulfonated aromatic and aliphatic hydrocarbons, sulfonated alpha-olefins, sulfated fatty alcohols and fatty alcohol ethers, sulfonated fatty acid methyl esters, sulfonated maleic acid esters, and carboxymethylated fatty alcohol polyglycol ethers. Examples of non-ionic surfactants include fatty alcohol ethoxylates, alkylphenol ethoxylates, fatty acid ethoxylates, fatty acid alkylolamides, fatty acid alkylolamide ethoxylates, fatty amine ethoxylates, and polyalkylene oxide block polymers. Cationic and amphoteric surfactants include quaternary ammonium compounds such as fatty amine carboxylates and betaines such as alkylampha-propinates and alkyl imidazolines, respectively.

The amount of surfactant in the aqueous mixture depends on the concentration of benzyl benzoate and solvent. Surfactants usually comprise from about 1% to about 20% of the aqueous mixture, but their relatively high cost, their tendency to leave a solid residue and their possible toxicity all limit their use. A useful concentrated aqueous miticide containing benzyl benzoate and benzyl alcohol contains about 12 wt. % of a surfactant. Studies show that less solvent is needed if a surfactant is used. For example, an aqueous miticide having a 1:1 weight ratio of benzyl alcohol to benzyl benzoate with a surfactant performs better than an aqueous miticide having a 2:1 weight ratio of benzyl alcohol to benzyl benzoate without a surfactant.

Since the disclosed miticide is an aqueous solution, it can be applied to carpets, bedding, upholstery and the like by any method suitable for applying liquids. One particularly advantageous method is to apply the miticide with a conventional deep cleaner or extraction cleaner. The deep cleaner evenly applies the aqueous miticide by spraying the aqueous mixture on carpeted areas so that the miticide can penetrate deep within the carpet pile. Preferably, the aqueous miticide is combined with a conventional cleaning solution to dissolve dirt and other contaminants, and dislodge materials that may either foster the growth of dust mites, such as human skin particles and animal dander, or cause an allergic reaction—dust mite fecal pellets and carcasses, for example.

After the aqueous miticide is sprayed on the carpet, about one half of the aqueous mixture is removed by vacuuming. Vacuuming also removes materials that may cause allergic reactions including dust mite fecal pellets and carcasses, dissolved dirt and other contaminants. Human skin particles and animal dander that are later ingested by dust mites readily absorb miticide that remains in the carpet after vacuuming. Thus, the aqueous miticide continues to kill dust mites long after the initial application. Unlike miticides adsorbed on solid carriers, the residual aqueous miticide is adsorbed on carpet fibers and is therefore available to taint dust mite food that finds its way onto the carpet after miticide application.

In addition to carpets, the aqueous miticide can be applied to other surfaces including draperies, bedding and upholstery using adapters that are typically provided with deep cleaners. Furthermore, the aqueous miticide can be applied to surfaces using conventional liquid spraying devices.

EXAMPLES

The follow examples are intended as illustrative and non-limiting, and represent specific embodiments of the present invention.

Example 1

An aqueous miticide was made by first dissolving 3.00 g of benzyl benzoate in. 10.10 g of ethyl alcohol at room temperature to form a clear, colorless solution. To this solution was added an additional 144.00 g of ethyl alcohol and 43.00 g of benzyl benzoate, resulting in an ethyl alcohol—benzyl benzoate premix comprising 77 wt. % ethyl alcohol and 23 wt. % benzyl benzoate. With stirring, 2.00 g of the ethyl alcohol—benzyl benzoate premix were added to 20.00 g of a surfactant, ethoxylated linear alcohol (40%) ethylene oxide, available under the trade name ALFONIC 810-40 Ethoxylate from Vista Chemical Corporation. To this solution was added, in turn and with stirring, 0.14 g of a surfactant, primary alkane sulfonate available under the trade name BIO-TERGE PAS-85 from Stepan Company, 5.00 g of EB glycol ether, 30.00 g of distilled water, 1.04 g of BIO-TERGE, four aliquots—4.99 g, 5.60 g, 1.94 g, 1.10 g—of distilled water, 1.85 g of EB glycol ether, and 1.3 g of BIO-TERGE. The resulting solution was clear and colorless. Table I lists the amounts of each component in the aqueous miticide.

TABLE 1

| Component | Amount, g | Weight Percent |
| --- | --- | --- |
| Benzyl Benzoate | 0.46 | 0.62 |
| Ethyl Alcohol | 1.54 | 2.05 |
| ALFONIC 810-40 Ethoxylate | 20.00 | 26.68 |
| BIO-TERGE PAS-85 | 2.48 | 3.31 |
| EB | 6.85 | 9.14 |
| Distilled Water | 43.63 | 58.20 |
| Total | 74.96 | 100.00 |

Example 2

An aqueous miticide was made by first dissolving 3.10 g of benzyl benzoate in. 11.00 g of isopropyl alcohol at room temperature to form a clear, colorless solution. To this solution was added an additional 143.10 g of isopropyl alcohol and 42.90 g of benzyl benzoate, resulting in an isopropyl alcohol—benzyl benzoate premix comprising 77 wt. % isopropyl alcohol and 23 wt. % benzyl benzoate. With stirring, 1.02 g of the isopropyl alcohol—benzyl benzoate premix were added to 10.00 g of a surfactant, ethoxylated linear alcohol (40%) ethylene oxide, available under the trade name ALFONIC 810-40 Ethoxylate from Vista Chemical Corporation. To this solution was added, in turn and with stirring, 0.52 g of a surfactant, primary alkane sulfonate available under the trade name BIO-TERGE PAS-85 from Stepan Company, and 2.52 g of EB glycol ether. Next, 29.00 g of distilled water was added in about 3 g aliquots, resulting in a clear solution. Table 2 lists the amounts of each component in the aqueous miticide.

TABLE 2

| Component | Amount, g | Weight Percent |
| --- | --- | --- |
| Benzyl Benzoate | 0.23 | 0.53 |
| Isopropyl Alcohol | 0.79 | 1.83 |
| ALFONIC 810-40 Ethoxylate | 10.00 | 23.22 |
| BIO-TERGE PAS-85 | 0.52 | 1.21 |
| EB | 2.52 | 5.85 |
| Water | 29.00 | 67.36 |
| Total | 43.06 | 100.00 |

Example 3

An aqueous miticide was made by first dissolving 3.01 g of benzyl benzoate in. 1.51 g of a surfactant, polyoxyethylene 20 sorbitan monolaurate, available under the trade name GLYCOSPERSE L-20 from Lonza, Inc., resulting in a clear, pale yellow solution. To this solution was added, with stirring, 1.50 g of another surfactant, ethoxylated aliphatic alcohol, available under the trade name CHEMAL TDA-9 from Chemax, Inc., 30.00 g of isopropyl alcohol, and 32.40 g of distilled water, resulting in a hazy solution. The hazy solution immediately cleared upon adding 17.10 g of isopropyl alcohol. Finally, an additional 14.43 g of distilled water and 0.15 g of fragrance were added to the solution, resulting in a clear, colorless solution. Table 3 lists the amounts of each component in the aqueous miticide.

TABLE 3

| Component | Amount, g | Weight Percent |
| --- | --- | --- |
| Benzyl Benzoate | 3.01 | 3.01 |
| Isopropyl Alcohol | 47.10 | 47.05 |
| GLYCOSPERSE L-20 | 1.51 | 1.51 |
| CHEMAL TDA-9 | 1.50 | 1.50 |
| Fragrance | 0.15 | 0.15 |
| Water | 46.83 | 46.78 |
| Total | 99.95 | 100.00 |

Example 4

An aqueous miticide was made by first dissolving 3.02 g of benzyl benzoate in 1.04 g of a surfactant, polyoxyethylene 20 sorbitan monolaurate, available under the trade name GLYCOSPERSE L-20 from Lonza, Inc., resulting in a clear, pale yellow solution. To this solution was added, with stirring, 3.00 g of another surfactant, ethoxylated aliphatic alcohol, available under the trade name CHEMAL TDA-9 from Chemax, Inc., 10.10 g of ethyl alcohol, and 7.33 g of distilled water, resulting in a hazy solution. The hazy solution immediately cleared upon adding 22.60 g of ethyl alcohol. Finally, an additional 2.03 g of GLYCOSPERSAL L-20 and 19.98 g of distilled water were added to the solution, resulting in a hazy, pale yellow solution. Table 4 lists the amounts of each component in the aqueous miticide.

TABLE 4

| Component | Amount, g | Weight Percent |
| --- | --- | --- |
| Benzyl Benzoate | 3.02 | 4.37 |
| Ethyl Alcohol | 32.70 | 47.33 |
| GLYCOSPERSE L-20 | 3.07 | 4.44 |
| CHEMAL TDA-9 | 3.00 | 4.34 |
| Water | 27.31 | 39.52 |
| Total | 69.10 | 100.00 |

Example 5

An aqueous miticide was made by first dissolving 1.50 g of benzyl benzoate in. 3.06 g of a surfactant, polyoxyethylene 20 sorbitan monolaurate, available under the trade name GLYCOSPERSE L-20 from Lonza, Inc., resulting in a clear, pale yellow solution. To this solution was added, with stirring, 1.02 g of another surfactant, ethoxylated aliphatic alcohol, available under the trade name CHEMAL TDA-9 from Chemax, Inc., 20.10 g of isopropyl alcohol, and 29.70 g of distilled water, resulting in a hazy solution. The hazy solution immediately cleared upon adding 0.50 g of isopropyl alcohol. Next, alternating aliquots of distilled water—0.48 g, 0.26 g, 10.19 g, 19.78 g—and isopropyl alcohol—0.50 g, 5.90 g, 10.50 g, 0.60 g— were added, with stirring, result in a clear, colorless solution. Table 5 lists the amounts of each component in the aqueous miticide.

TABLE 5

| Component | Amount, g | Weight Percent |
| --- | --- | --- |
| Benzyl Benzoate | 1.50 | 1.44 |
| Isopropyl Alcohol | 38.10 | 36.60 |
| GLYCOSPERSE L-20 | 3.06 | 2.94 |
| CHEMAL TDA-9 | 1.02 | 0.98 |
| Water | 60.41 | 58.04 |
| Total | 104.09 | 100.00 |

Example 6

An aqueous miticide was made by first dissolving 3.05 g of benzyl benzoate in. 5.86 g of a surfactant, polyoxyethylene 20 sorbitan monolaurate, available under the trade name GLYCOSPERSE L-20 from Lonza, Inc., resulting in a clear, pale yellow solution. To this solution was added, with stirring, 1.99 g of another surfactant, ethoxylated aliphatic alcohol, available under the trade name CHEMAL TDA-9 from Chemax, Inc., 80.00 g of isopropyl alcohol, 0.30 g of fragrance, and 108.93 g of distilled water, resulting in a clear, pale yellow solution. Table 6 lists the amounts of each component in the aqueous miticide.

TABLE 6

| Component | Amount, g | Weight Percent |
|---|---|---|
| Benzyl Benzoate | 3.05 | 1.52 |
| Isopropyl Alcohol | 80.00 | 39.97 |
| GLYCOSPERSE L-20 | 5.86 | 2.93 |
| CHEMAL TDA-9 | 1.99 | 0.99 |
| Fragrance | 0.30 | 0.15 |
| Water | 108.93 | 54.44 |
| Total | 200.13 | 100.00 |

Example 7

Dust mite kill rate for benzyl alcohol was determined. Benzyl alcohol was diluted 1:10 with acetone. Two hundred fifty μl of the benzyl alcohol—acetone solution was applied to a 5 cm diameter filter paper disk. The acetone was evaporated off, leaving 25 μl of benzyl alcohol on an area of 19.63 cm$^2$. Dust mites were placed in contact with the disk, resulting in a 100% kill rate.

Example 8

Dust mite kill rate for an aqueous benzyl alcohol mixture was determined. Ten ml of benzyl alcohol was dissolved in 1000 ml of BISSEL, CARPET CARE detergent, which contains surfactants and about 85 wt. % water. The clear solution was diluted 1:10 with distilled water, and 250 μl of the resulting mixture was applied to a 5 cm diameter filter paper disk. The filter paper was allowed to dry at room temperature, leaving behind about 0.25 μl of benzyl alcohol on an area of 19.63 cm$^2$. Dust mites were placed in contact with the disk, resulting in about an 80% kill rate of the dust mites.

Example 9

Dust mite kill rate for an aqueous benzyl alcohol mixture was determined. Ten ml of benzyl alcohol was dissolved in 1000 ml of BISSEL CARPET CARE ALLERGEN CONTROL, which contains surfactants and about 80 wt. % water. The clear solution was diluted 1:10 with distilled water, and 250 μl of the resulting mixture was applied to a 5 cm diameter filter paper disk. The filter paper was allowed to dry at room temperature, leaving behind about 0.25 μl of benzyl alcohol on an area of 19.63 cm$^2$. Dust mites were placed in contact with the disk, resulting in about an 80% kill rate of the dust mites.

It is to be understood that the above description is intended to be illustrative and not restrictive. Many reasonable variations and modifications are possible and will be apparent to those of skill in the art upon reading the above description. The scope of the invention should, therefore, be determined not with reference to the above description, but should instead be determined with reference to the appended claims, along with the full scope of equivalents to which such claims are entitled.

What is claimed is:

1. An aqueous mixture comprising:
   benzyl benzoate in an amount effective for killing dust mites; in an amount of benzyl alcohol sufficient to solubilize the benzyl benzoate;
   a surfactant; and
   water;
   wherein the amounts of benzyl alcohol, surfactant, benzyl benzoate and water are selected to maintain a stable dispersion of benzyl benzoate in the aqueous mixture; and
   wherein the benzyl benzoate and the benzyl alcohol together comprise from about 0.01% to about 5% of the aqueous mixture by weight.

2. The aqueous mixture of claim 1 wherein the aqueous mixture is transparent.

3. The aqueous mixture of claim 1 wherein the ratio of benzyl alcohol to benzyl benzoate is in a range of about 5:1 to about 1:5 by weight.

4. The aqueous mixture of claim 3 wherein the ratio of benzyl alcohol to benzyl benzoate is about 2:1.

5. The aqueous mixture of claim 1 wherein the benzyl benzoate and the benzyl alcohol together comprise from about 1.0% to about 5.0% of the aqueous mixture by weight.

6. The aqueous mixture of claim 1 wherein the surfactant comprises from about 1% to about 20% by weight of the aqueous mixture.

7. The aqueous mixture of claim 6 wherein water comprises at least 40% by weight of the aqueous mixture.

8. The aqueous mixture of claim 1 wherein water comprises at least 40% by weight of the aqueous mixture.

9. An aqueous mixture consisting essentially of:
   about 0.5 to about 5% by weight of benzyl benzoate in an amount effective for killing dust mites;
   a solvent having a high affinity for benzyl benzoate and for water in an amount sufficient to solubilize the benzyl benzoate;
   a surfactant in an amount of about 1% to about 20% by weight of the aqueous mixture; and
   at least about 40 wt. % water;
   wherein the amounts of solvent, surfactant and water are selected to maintain a stable dispersion of benzyl benzoate and solvent in the aqueous mixture.

10. The aqueous mixture of claim 9 wherein the aqueous mixture is transparent.

11. The aqueous mixture of claim 9 wherein the solvent is a miticide.

12. The aqueous mixture of claim 9 wherein the solvent is an aliphatic alcohol, an aromatic alcohol, or a glycol ether, alone or in combination.

13. The aqueous mixture of claim 12 wherein the solvent is isopropyl alcohol or ethyl alcohol, alone or in combination.

14. The aqueous mixture of claim 12 wherein the solvent is benzyl alcohol.

15. The aqueous mixture of claim 14 wherein the ratio of benzyl alcohol to benzyl benzoate is in a range of about 5:1 to about 1:5 by weight.

16. The aqueous mixture of claim 15 wherein the ratio of benzyl alcohol to benzyl benzoate is about 1:1.

17. The aqueous mixture of claim 14 wherein the benzyl benzoate and the benzyl alcohol comprise from about 0.01% to about 5% of the aqueous mixture by weight.

18. The aqueous mixture of claim 17 wherein the benzyl benzoate and the benzyl alcohol together comprise from about 1.0% to about 5.0% of the aqueous mixture by weight.

19. The aqueous mixture of claim 9 wherein the surfactant is a lipophillic surfactant, a hydrophobic surfactant, an anionic, a non-ionic, a cationic or an amphoteric surfactant, alone or in combination.

20. The aqueous mixture of claim 9 wherein the surfactant comprises about 12% of the aqueous mixture by weight.

21. A method for killing dust mites on a surface comprising the step of applying an aqueous mixture to the surface;
   wherein the aqueous mixture consists essentially of:
      about 0.5 to about 5% by weight of benzyl benzoate in an amount effective for killing dust mites;

a solvent having a high affinity for benzyl benzoate and for water in an amount sufficient to solubilize the benzyl benzoate;

a surfactant in an amount of about 1% to about 20% by weight of the aqueous mixture; and at least about 40 wt. % water;

wherein the amounts of solvent, surfactant and water are selected to maintain a stable dispersion of benzyl benzoate and solvent in the aqueous mixture.

22. The method of claim 21 wherein the solvent is an aliphatic alcohol, an aromatic alcohol, or a glycol ether, alone or in combination.

23. The method of claim 22 wherein the solvent is isopropyl alcohol or ethyl alcohol, alone or in combination.

24. The method of claim 22 wherein the solvent is benzyl alcohol.

25. The method of claim 24 wherein the ratio of benzyl alcohol to benzyl benzoate is in a range of about 5:1 to about 1:5 by weight.

26. The method of claim 25 wherein the ratio of benzyl alcohol to benzyl benzoate is about 2:1.

27. The method of claim 26 wherein the benzyl benzoate and the benzyl alcohol together comprise from about 0.01% to about 5% of the aqueous mixture by weight.

28. The method of claim 27 wherein the benzyl benzoate and the benzyl alcohol comprise from about 1.0% to about 5.0% of the aqueous mixture by weight.

29. The method of claim 21 wherein the surfactant is a lipophillic surfactant, a hydrophobic surfactant, an anionic, a non-ionic, cationic or an amphoteric surfactant, alone or in combination.

30. The method of claim 21 wherein the surfactant comprises about 12% of the aqueous mixture by weight.

31. The method of claim 21 wherein the surface is a carpet surface.

32. The method of claim 21 wherein the surface is a bedding surface.

33. The method of claim 21 wherein the surface is an upholstered surface.

* * * * *